United States Patent [19]

Stopp et al.

[11] Patent Number: 4,508,920
[45] Date of Patent: Apr. 2, 1985

[54] PROCESS FOR THE PREPARATION OF AROMATIC HYDROXYCARBOXYLIC ACIDS

[75] Inventors: Gerhard Stopp, Leverkusen; Horst Karkossa, Leichlingen; Viktor Trescher, Leverkusen, all of Fed. Rep. of Germany

[73] Assignee: Bayer Aktiengesellschaft, Leverkusen, Fed. Rep. of Germany

[21] Appl. No.: 472,501

[22] Filed: Mar. 7, 1983

[30] Foreign Application Priority Data

Mar. 23, 1982 [DE] Fed. Rep. of Germany ....... 3210597

[51] Int. Cl.$^3$ ............................................. C07C 51/15
[52] U.S. Cl. .................................... 562/423; 562/424; 562/425
[58] Field of Search ........................ 562/423, 424, 425

[56] References Cited

U.S. PATENT DOCUMENTS 4,287,357  9/1981  Mueller .............................. 562/425

Primary Examiner—Paul J. Killos
Attorney, Agent, or Firm—Sprung, Horn, Kramer & Woods

[57] ABSTRACT

Aromatic hydroxycarboxylic acids are prepared by reacting alkali metal salts of aromatic hydroxy compounds in the solid phase with carbon dioxide in a process in which the alkali metal salt of the aromatic hydroxy compound is reacted at temperatures of 120° to 300° C., in the form of granules, in a fluidized bed with carbon dioxide, if appropriate under elevated pressure and, if appropriate, in the presence of the aromatic hydroxy compound in the form of vapor, with continuous removal, by means of excess carbon dioxide, of the aromatic hydroxy compound which is formed, until at least 40% of the hydroxy compound have been converted into the alkali metal salt of the corresponding hydroxycarboxylic acid, and, if appropriate, the resulting alkali metal salt of the hydroxycarboxylic acid is reacted further in a subsequent stage at temperatures of 150° to 300° C. and under elevated pressure, in the presence of carbon dioxide, with the aromatic hydroxy compound formed, and the resulting reaction product is then converted in a customary manner into the free acid.

10 Claims, No Drawings

PROCESS FOR THE PREPARATION OF AROMATIC HYDROXYCARBOXYLIC ACIDS

The invention relates to a process for the preparation of an aromatic hydrocarboxylic acid by reacting an alkali metal salt of an aromatic compound in the solid phase with carbon dioxide.

CROSS REFERENCE TO RELATED APPLICATION

This application is related to one filed concurrently herewith entitled Process for Preparing Aromatic Hydroxycarboxylic Acids, assigned to the assignee hereof.

The conversion of alkali metal salts of aromatic hydroxy compounds in the solid form, by means of carbon dioxide, into the alkali metal salts of the corresponding aromatic hydroxycarboxylic acids is known. Thus, for example, German 960,206 claims a process for the conversion of finely granular alkali metal salts of aromatic monohydroxy compounds into the alkali metal salts of the corresponding hydroxycarboxylic acids by means of carbon dioxide, which is characterized in that the starting salts are employed in the form of particles having a dimeter of 20 to 200 $\mu$m, and are treated with carbon dioxide gas in a state similar to that of a liquid, a so-called fluidized bed.

Furthermore, it is known from German Auslegeschrift 1,493,881 to prepare p-hydroxybenzoic acid by reacting potassium phenate at a temperature of 190° to 210° C. and under a pressure of up to 6 atmospheres gauge, using a recycle mixture, which has been brought to reaction temperature, consisting of carbon dioxide and an inert gas, care being taken continually to remove the heat of reaction and the phenol formed and the carbon dioxide consumed being replaced by fresh gas, and the potassium phenate being employed in the form of anhydrous granules or briquettes having a diameter or length of side not exceeding 30 mm. The reaction takes place in this case in a solid bed reactor which is charged with the potassium phenate and in which the gas is passed upwards.

British Pat. No. 1,205,447 also describes a process for the preparation of alkali metal salts of aromatic hydroxycarboxylic acids by reacting carbon dioxide at a fairly high temperature with pulverulent alkali metal phenates having a diameter less than 70 $\mu$m.

Disadvantages in the processes known from the state of the art are the yields, which are unsatisfactory in some cases, of aromatic hydroxycarboxylic acids (German Auslegeschrift 1,493,881 and British Pat. No. 1,205,447), the problems which arise when using a pulverulent starting material, together with the handling of the pulverulent material, which, for safety reasons, is associated with a considerable technical effort (German 960,206 and British Pat. No. 1,205,447), and the use, which is accompanied by a loss of carbon dioxide and exhaust air problems, of inert gas for cooling and for removing the phenol formed during the reaction (German Auslegeschrift 1,493,881). A further disadvantage in the case of the process of German Patent Specification 960,206 is that, under the reaction conditions described there, the free aromatic hydroxy compound is formed and is not retained, even by absorptive additives, such as kaolin, and thus leads to caking and agglutination of the reaction products.

A process has now been found for the preparation of aromatic hydroxycarboxylic acids by reacting alkali metal salts of aromatic hydroxy compounds in the solid phase with carbon dioxide, which is characterized in that the alkali metal salt of the aromatic hydroxy compound is reacted at temperatures of 120° to 300° C., in the form of granules, in a fluidized bed with carbon dioxide, with continuous removal, by means of excess carbon dioxide, of the aromatic hydroxy compound which is formed, until at least 40% of the hydroxy compound have been converted into the alkali metal salt of the corresponding hydroxycarboxylic acid, and, if desired, the resulting alkali metal salt of the hydroxycarboxylic acid is reacted further in a subsequent stage at temperatures of 150° to 300° C. and under elevated pressure, in the presence of carbon dioxide, with the aromatic hydroxy compound formed, and the resulting reaction product is then converted into the free acid. The reaction at 120° to 300° C. can, if desired, be carried out under pressure and/or, if desired, in the presence of aromatic hydroxy compound in the vapor state, following the process, the salt can be converted into the free acid by customary methods.

Alkali metal salts of aromatic hydroxy compounds which can be employed in the process according to the invention are the sodium and/or potassium salts of phenol, cresols, naphthols, 2-hydroxycarbazole or 3-hydroxydiphenylene oxide. The aromatic hydroxy compounds can be monosubstituted or polysubstituted by lower alkyl, such as methyl, ethyl or tert.-butyl, and by halogens, such as fluorine, chlorine or bromine, preferably chlorine. It is preferable to employ in the process according to the invention sodium phenate, the sodium salts of cresols and the sodium salts of chlorophenols, particularly preferably sodium phenate.

The alkali metal salts of the aromatic hydroxy compounds are employed in the process according to the invention in the form of anhydrous granules having a diameter of about 0.2 to 5 mm, preferably 0.3 to 4 mm, and a specific surface area of 1 to 6 m$^2$/g, preferably 2 to 4 m$^2$/g (surface area determined by the BET method/DIN 66,132).

The granules to be used according to the invention can be prepared using an own, earlier process, which is described in, the disclosure of which is hereby incorporated herein by reference.

In the process according to the invention, the granulated salts of the aromatic hydroxy compounds are reacted in a fluidized bed with the carbon dioxide, which can, if desired, contain the free aromatic hydroxy compound in the form of vapour. In this process the carbon dioxide is circulated, the heat of reaction and the aromatic hydroxy compound formed during the reaction being removed by means of excess carbon dioxide. The aromatic hydroxy compound can be removed, for example by cooling from the carbon dioxide which is circulated. The amount of carbon dioxide which has been consumed during the reaction is added to the circulated carbon dioxide.

The reaction is carried out in the fluidized bed at temperatures of about 120° to 300° C., preferably at 150° to 250° C. The pressures in the reaction are about 1 to 50 bar, absolute, preferably 1 to 6 bar, absolute.

After about 40%, preferably 40 to 50%, of the aromatic hydroxy compound have reacted with the carbon dioxide to give the alkali metal salt of the corresponding hydroxycarboxylic acid, the reaction can be terminated and the reaction product then obtained can be converted in a customary manner into the free acid.

In the case of some salts of the aromatic hydroxy compounds, such as sodium phenate and sodium cresylate, it has proved advantageous to subject the resulting alkali metal salt of the corresponding hydroxycarboxylic acid to a further reaction, in a subsequent stage, in the presence of carbon dioxide at temperatures of 150° to 300° C., preferably at temperatures of 160° to 240° C., and under pressures of 2 to 50 bar, absolute, preferably at 4 to 10 bar, absolute, to a further reaction with the aromatic hydroxy compound formed, that is to say until no more carbon dioxide is absorbed. Moreover, in the subsequent stage, it is also possible to add an additional quantity of the appropriate aromatic hydroxy compound (about 5 to 15 mol %) apart from the aromatic hydroxy compound which has already been formed.

This subsequent stage can also be carried out in another apparatus, such as a stirred vessel or a screw machine, instead of a fluidized bed.

In order to work up the reaction mixture, excess aromatic hydroxy compound is, if necessary, removed from the reaction mixture by vacuum distillation, water is then added to the reaction mixture and the latter is neutralized and, if necessary, clarified by introducing additives, such as active charcoal, and is precipitated with mineral acids, such as sulphuric acid or hydrochloric acid, whereby the free aromatic hydroxycarboxylic acid is obtained.

The process according to the invention can be carried out as follows (illustrated using the preparation of salicylic acid as an example): the dry granules of sodium phenate are fed continuously to the fluidized bed reactor and are reacted continuously, at about 140° to 170° C. and under a pressure of about 5 to 10 bar absolute, with the carbon dioxide containing phenol, which flows upwards and is recycled. In the course of this, the carbon dioxide used as the circulating gas, which is used to remove the phenol formed and to carry off the heat of reaction, is replenished with the appropriate quantity of carbon dioxide which has been consumed in the reaction with the hydroxy compound. After the sodium phenate has taken up approx. 50% of the theoretically possible quantity of carbon dioxide, the resulting sodium salt of salicyclic acid is transferred to a stirred vessel and is subjected there, in the presence of carbon dioxide and at temperatures of about 160° to 210° C. and under a pressure of about 5 to 10 bar, absolute, to a further reaction with the phenol which has been formed, a further approx. 10 mol % of phenol being added.

Residual quantities of phenol are removed from the reaction mixture in a subsequent vacuum distillation (approx. 0.01 bar, absolute), and the reaction mixture is then dissolved in water and 50% strength sulphuric acid is added, whereupon the free salicylic acid is obtained. The yields of aromatic hydroxycarboxylic acids achieved in the process according to the invention are about 50 to 96% of theory, relative to the starting compound, depending on the alkali metal salt of the aromatic hydroxy compound employed.

The process according to the invention can be carried out continuously as well as discontinuously.

The advantages of the process according to the invention can be seen particularly in the avoidance of a liquid phenolic phase, as a result of which agglutination and caking of the reaction products are prevented. Substantially shortened reaction times are achieved thereby, at a low consumption of energy. The formation of by-products can be minimized because it is possible to control the temperature accurately. In addition, discolorations of the reaction products caused by aerial oxidation can be avoided in the process according to the invention. Finally, the aromatic hydroxycarboxylic acids are obtained in good yields and with a high selectivity in the process according to the invention.

A particularly surprising factor in the process according to the invention is that the granules treated in the fluidized bed remain in the solid form even after the reaction with the carbon dioxide and can thus be removed from the fluidized bed reactor without problems. The granular form is also retained when completing the reaction by carrying it out at elevated temperatures, which is particularly advantageous for carrying out the process according to the invention on an industrial scale and also for processing the reaction products further. A further surprising factor is that, in spite of the alkali metal salts of aromatic hydroxy compounds being employed in a coarsely granular form, the reaction rate and the yield are not adversely impaired, although reference is made in Ind. J. Technol. Vol. 11, page 187 (1973) to the fact that the reaction rate of the carboxylation decreases as the particle size of the sodium phenate increases.

The aromatic hydroxycarboxylic acids prepared by the process according to the invention are valuable intermediate products for the preparation of dyestuffs, medicaments, plant protection agents, tanning substances and cosmetics (Ullmanns Encycl. d. techn. Chemie ("Ullmann's Encyclopaedia of Industrial Chemistry") Volume 3, 4th Edition, pages 163–168).

The examples which follow are intended to illustrate the process according to the invention without, however, limiting it to these examples.

EXAMPLE 1

A continuous stream of 8 parts/hr. of dry, granulated potassium phenate (diameter of major portion: 0.6 to 1.2 mm) is introduced into a fluidized bed via a suitable feeding device. The fluidizing gas used is carbon dioxide, which is at the same time the reaction gas. The reaction gas is circulated. The pressure is 1.5 bar, absolute. When the potassium phenate enters the carbon dioxide atmosphere, phenol is split off spontaneously, and is distributed within the fluidized bed and vaporized. It is discharged with the recycle gas and is removed from the latter by cooling. Carbon dioxide, which has been substantially freed from phenol, is then recycled to the fluidized bed. The temperature within the fluidized bed is kept at 240° C.

6.5 parts/hr. of dipotassium p-hydroxybenzoate are obtained at a dwell time of not more than 40 minutes. This quantity is withdrawn continuously from the bed in the form of granules. The yield of p-hydroxybenzoic acid, relative to the phenol consumed, is over 98%. The salt has a high purity and can be converted into the free acid in a customary manner by means of mineral acids.

EXAMPLE 2

A continuous stream of 5.0 parts/hr. of granulated, dry sodium α-naphtholate is introduced into a fluidized bed. The fluidizing gas used is carbon dioxide, which is recycled and kept at a constant pressure of 5 bar, absolute. The carbon dioxide consumed in the reaction is replenished via the maintenance of the pressure.

A temperature of 150° C. is maintained in the fluidized bed, the heat of reaction being removed by the recycle gas. Approx. 70% of the naphtholate react with carbon dioxide. A continuous stream of granules is withdrawn from the fluidized bed at a dwell time of 5 to 20 minutes and is fed to a subsequent fluidized bed. In the latter, the reaction is carried to completion at 170° C. under a recycle gas stream of carbon dioxide at a pressure of 4.8 bar, absolute. Small quantities of unreacted naphthol are recovered from the recycle gas by cooling.

The reaction granules are withdrawn continuously from this second fluidized bed at a dwell time of less than 10 minutes and are passed over a cooling range. 6.0 parts of the sodium salt of 1-hydroxynaphthalene-2-carboxylic acid are obtained, corresponding to a yield of 95%.

The reaction product has a high degree of purity and can be processed further directly as an intermediate product, or it is dissolved in water in a customary manner, neutralized, clarified and converted into the free acid by means of mineral acids.

What is claimed is:

1. In a process for the preparation of an aromatic hydrocarboxylic acid by contacting alkali metal salt of an aromatic hydroxy compound in the solid phase with carbon dioxide, and thereafter converting the resultant reaction product to the free acid, the improvement which comprises contacting said alkali metal salt of said aromatic hydroxy compound in the form of granules having a diameter of 0.2 to 5 mm and a specific surface area of 1 to 6 $m^2$ per gram in a fluidized bed with carbon dioxide at a temperature of 120° to 300° C. with continuous removal, by means of excess carbon dioxide, of the aromatic hydroxy compound which is formed, until at least 40% of said alkali metal salt with aromatic hydroxy compound has been converted into the alkali metal salt with the corresponding hydroxycarboxylic acid, the process being carried out employing a reaction mixture consisting essentially of said alkali metal salt of aromatic hydroxy compound and said carbon dioxide.

2. A process according to claim 1, wherein said alkali metal salt of an aromatic hydroxy compound is a sodium and/or potassium salt of phenol, a cresol, a naphthol, 2-hydroxycarbazole or 3-hydroxycarbazole.

3. A process according to claim 1, wherein said alkali metal salt of aromatic hydroxy compound is in the form of granules having a diameter of 0.3 to 4 mm and a specific surface area of 2 to 4 $m^2$ per gram.

4. A process according to claim 1, wherein the reaction in the fluidized bed is carried out under elevated pressure.

5. A process according to claim 1, wherein the reaction in the fluidized bed is carried out in the presence of aromatic hydroxy compounds in the vapor state.

6. A process according to claim 1, wherein the reaction is carried out under a pressure of 1 to 50 bar, absolute.

7. A process according to claim 1, wherein the fluidized bed reaction is carried out at a temperature of 150°–300° C.

8. A process according to claim 1, wherein the fluidized bed reaction is carried out until between 40 and 50% of the alkali metal salt of aromatic hydroxy compound has been converted into the alkali metal salt of the corresponding hydroxycarboxylic acid.

9. A process according to claim 1, wherein the reaction of the subsequent stage is carried out under pressure of 2 to 50 bar, absolute.

10. A process according to claim 1, wherein the resulting alkali metal salt of the hydroxycarboxylic acid is reacted further, in the presence of carbon dioxide, with the aromatic hydroxy compound, which is formed, in a subsequent stage at a temperature of 150° to 300° C. under pressure.

* * * * *